United States Patent
Masumoto

(10) Patent No.: US 9,495,794 B2
(45) Date of Patent: Nov. 15, 2016

(54) THREE-DIMENSIONAL IMAGE DISPLAY APPARATUS, METHOD, AND PROGRAM

(71) Applicant: FUJIFILM Corporation, Tokyo (JP)

(72) Inventor: Jun Masumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/644,386

(22) Filed: Mar. 11, 2015

(65) Prior Publication Data

US 2015/0187118 A1  Jul. 2, 2015

Related U.S. Application Data

(63) Continuation of application No. PCT/JP2013/005328, filed on Sep. 9, 2013.

(30) Foreign Application Priority Data

Sep. 13, 2012  (JP) .................................. 2012-201581

(51) Int. Cl.
| | |
|---|---|
| G06T 15/08 | (2011.01) |
| G06T 7/00 | (2006.01) |
| G06T 19/00 | (2011.01) |
| A61B 6/03 | (2006.01) |
| A61B 6/00 | (2006.01) |

(52) U.S. Cl.
CPC ............... *G06T 15/08* (2013.01); *A61B 6/468* (2013.01); *G06T 7/0012* (2013.01); *G06T 19/00* (2013.01); *A61B 6/032* (2013.01); *A61B 6/466* (2013.01); *G06T 2219/004* (2013.01)

(58) Field of Classification Search
None
See application file for complete search history.

(56) References Cited

U.S. PATENT DOCUMENTS

| | | | |
|---|---|---|---|
| 6,904,392 B1 * | 6/2005 | Marty | .................... G06T 19/00 345/651 |
| 2004/0101175 A1 | 5/2004 | Yarger et al. | |
| 2005/0116964 A1 | 6/2005 | Kotake et al. | |
| 2010/0079455 A1 | 4/2010 | Wei et al. | |
| 2010/0128963 A1 | 5/2010 | Waku et al. | |

(Continued)

FOREIGN PATENT DOCUMENTS

| | | | |
|---|---|---|---|
| JP | 2001-195610 A | 7/2001 |
| JP | 2004-174248 A | 6/2004 |

(Continued)

OTHER PUBLICATIONS

Y. Sato et al., "Extraction of Lung Lobes in X-ray CT images and its Application to Evaluation of Heavy Ion Radiation Therapy", Medical Imaging Technology, Nov. 2004, pp. 269-277, vol. 22, No. 5.

(Continued)

*Primary Examiner* — Said Broome
(74) *Attorney, Agent, or Firm* — Sughrue Mion, PLLC

(57) ABSTRACT

A label adding unit adds labels to structures such as a body surface region, a lung region, bronchi, and pulmonary nodules of a human extracted by a structure extraction unit from a three-dimensional image of a chest. An image display control unit displays the three-dimensional image by volume rendering on a display unit. At this time, a label display determination unit determines at least one label to be displayed with the volume rendering image to be displayed based on the opacity during the volume rendering display. A label display control unit displays the determined label with the volume rendering image on the display unit.

8 Claims, 4 Drawing Sheets

(56) References Cited

U.S. PATENT DOCUMENTS

| | | |
|---|---|---|
| 2010/0293505 A1 | 11/2010 | Kiefer et al. |
| 2011/0085701 A1 | 4/2011 | Kitamura |
| 2011/0228997 A1 | 9/2011 | Sharp et al. |
| 2011/0286630 A1* | 11/2011 | Harder .................... G06T 15/08 382/103 |

FOREIGN PATENT DOCUMENTS

| | | |
|---|---|---|
| JP | 2005148409 A | 6/2005 |
| JP | 2010-500089 A | 1/2010 |
| JP | 2010-148866 A | 7/2010 |
| JP | 2010-220742 A | 10/2010 |
| JP | 2011-098195 A | 5/2011 |
| JP | 2011-206168 A | 10/2011 |
| JP | 2011-212314 A | 10/2011 |
| JP | 2012-075645 A | 4/2012 |

OTHER PUBLICATIONS

N. Kawamura et al., "Examination of Bronchus Extraction Algorithm using Multi Slice CT Images", The Institute of Electronics, Information and Communication Engineers, Technical Report, MBE, ME and bio-cybernetics, 2005, pp. 11-14, vol. 105, No. 221.

K. Mori et al., "A method for automated nomenclature of bronchial branches extracted from CT images", International Congress Series, 2005, pp. 86-91, vol. 1281.

Y. Li et al., "Interactive Segmentation of Lung Nodules using AdaBoost and Graph Cuts", Fourth International Workshop on Pulmonary Image Analysis, pp. 125-133.

C. Schneider et al., "Automated lung nodule detection and segmentation", Medical Imaging, Proc. of SPIE, 2009, pp. 72601T-1-72601T-8, vol. 7260.

J. Masumoto et al., "Automated Liver Segmentation Method for Dynamic CT Data Using Non-Rigid Registration", Journal of Computer Aided Diagnosis of Medical Images, Jun. 2003 pp. 29-38, vol. 7, No. 4-1.

P.S. Sulaiman et al., "A Liver Level Set (LLS) Algorithm for Extracting Liver's Volume Containing Disconnected Regions Automatically", IJCSNS International Journal of Computer Science and Network Security, Dec. 2008, pp. 246-252, vol. 8, No. 12.

T. Hitosugi et al., "Development of a liver extraction method using a level set method and its performance evaluation", Computer Aided Diagnosis of Medical Images, Jun. 2003, pp. 1-9, vol. 7, No. 4-2.

M. Freiman et al., "Liver tumors segmentation from CTA images using voxels classification and affinity constraint propagation", Int J CARS, Jun. 24, 2010.

Internationsl Search Report of PCT/JP2013/005328 dated Nov. 12, 2013.

Communication dated Nov. 4, 2015 from the Japanese Patent Office in counterpart application No. 2012-201581.

Communication dated Jan. 14, 2016, issued by the Australian Patent Office in corresponding application No. 2013317201.

Communication dated Apr. 25, 2016 issued by the Canadian Intellectual Property Office in counterpart application No. 2884679.

Communication dated May 23, 2016, from the European Patent Office in counterpart European Application No. 13837633.0.

Communication dated May 31, 2016, from the Japanese Patent Office in counterpart application No. 2012-201581.

* cited by examiner

THREE-DIMENSIONAL IMAGE DISPLAY APPARATUS, METHOD, AND PROGRAM

CROSS-REFERENCE TO RELATED APPLICATIONS

This application is a Continuation of PCT International Application No. PCT/JP2013/005328 filed on Sep. 9, 2013, which claims priority under 35 U.S.C. §119(a) to Japanese Patent Application No. 2012-201581 filed on Sep. 13, 2012. Each of the above applications is hereby expressly incorporated by reference, in its entirety, into the present application.

BACKGROUND OF THE INVENTION

1. Field of the Invention

The present invention relates to a three-dimensional display apparatus and a three dimensional display method for displaying a volume rendering image of a three-dimensional image composed of a plurality of tomographic images which have been obtained by tomographic imaging of an object, as well as a program for causing a computer to execute the three-dimensional image display method.

2. Description of the Related Art

In recent years, three-dimensional images of high quality are increasingly used for diagnostic imaging, accompanying advances in medical instruments (for example, multi-detector CT's, and the like). Further, analysis of such three-dimensional image facilitates grasping the three-dimensional shapes of various organs present in the interior of the body, and further enables the relative positional relationships among the respective tissues of arteries, veins, and tumors present in the organs and three-dimensional structures thereof to be understood. In such a case, a specific organ and a specific structure in the organ are extracted by using various image processing algorithms and a three-dimensional shape is projected onto a two-dimensional plane by display method such as volume rendering (VR) and the like so that the three-dimensional structure thereof can be understood.

Here, when the three-dimensional display is displayed by VR, an organ, a tissue, a structure, and the like of interest are extracted, and a color (R, G, B) and an opacity level (opacity) are set for the signal value of each pixel, based on the signal value (a CT value if the image is a CT image) at each voxel position in the three-dimensional image of the extracted structure. In such a case, color templates, in each of which a color and an opacity level are set according to a region of interest, are preliminarily prepared, and a desired color template is selected depending on regions. This enables a region of interest to be visualized in a volume rendering image (VR image).

Meanwhile, there are also cases in which arrows that indicate the presence of tumors, text indicating the name of each structure included in three-dimensional images, and the like are added to the position of a corresponding structure as a label. Further, a method in which a spine is extracted and a label is automatically added to the extracted spine, and a method in which a bronchus is extracted and an anatomical medical term is added to the extracted bronchus as a label have been proposed.

A method in which when displaying each of the three-dimensional images, to which labels are added in such a manner as described above, text described in each label is displayed by pointing to a position where the label is added has been proposed (refer to Patent Document 1 (PCT Japanese Publication No. 2010-500089)). In this method, the text includes the name of a segmented anatomical structure, descriptions thereof, or abnormality thereof. Further, a method in which while a doctor makes an observation by using three-dimensional images and examines a subject by utilizing an endoscope, a label on which the doctor's observation is described is displayed on an endoscopic image being displayed in the case that the endoscope approaches the position to which the observation is added has been proposed (refer to Patent Document 2 (Japanese Unexamined Patent Publication No. 2011-206168)).

SUMMARY OF THE INVENTION

In the case that a small number of structures are included in a three-dimensional image, it is possible to display all of the labels without any problems because there are a small number of labels added to the structures. However, in the case that labels are added to all of the various structures which are objects contained over a wide range in a three-dimensional image, such as a chest or a chest and abdominal part of the human body, there is a possibility that all labels cannot be displayed on a display screen when the three-dimensional image is displayed. Further, in the case that all of the labels are displayed, the labels added to the structures in the interior of the organs are displayed in a state that only the appearance of the organs are visualized and the interiors of the organs cannot be viewed. Therefore, it is impossible to understand to which structure the labels are added. That is, there is no point in displaying the labels in such a case. In this case, it can be considered to automatically switch between a display mode or a non-display mode of each label according to the structures visualized in a three-dimensional image. However, in the case that there are many structures contained in a three-dimensional image, it is extremely troublesome to perform such an operation because there are a large number of labels.

The present invention has been developed in view of the foregoing circumstance. It is an object of the present invention to enable the display of labels added to a three-dimensional image to be controlled without imposing a burden on a user.

A three-dimensional image display apparatus according to the present invention that displays a three-dimensional image of an object composed of a plurality of structures, to each of which at least one label is added, comprising:

an image display control means that displays the three-dimensional image by volume rendering;

a label display determination means that determines at least one label to be displayed from a plurality of labels based on the opacity of the three-dimensional image to be displayed by volume rendering;

a label display control means that adds at least one label determined to be displayed to a corresponding structure and displays the label with the three-dimensional image to be displayed by volume rendering.

The structures refer to various structures contained in the object represented by the three-dimensional image. For example, in the case of a three-dimensional image of a human body, the structures are not limited to structures, such as tumors and various organs (a lung, a liver, a heart, a spleen, a pancreas, and the like) in the interior of a human body, which constitute a specific region. The structures also include specific positions, such as the center positions of tumors, vascular bifurcations, and the center points of various organs.

Note that in the three-dimensional image display apparatus according to the present invention, the label display determination means may determine that labels added to structures are to be displayed in the case that the distance between a position at which the three-dimensional image becomes opaque according to the opacity thereof and a structure to which a label has been added is less than or equal to a specified value.

Further, in the three-dimensional image display apparatus according to the present invention, the label display control means may be means that controls the position of the at least one label to be displayed for each structure when the at least one label determined to be displayed is added to a plurality of structures.

Further, in the three-dimensional image display apparatus according to the present invention, the label display control means may cause the at least one label to be added only to a portion having a specified area or greater and displayed when the structure is divided into a plurality of portions having the identical label to be displayed and is present in the three-dimensional image to be displayed by volume rendering.

Further, in the three-dimensional image display apparatus according to the present invention, the label display control means may be means that causes the at least one label to be added only to a portion having the largest area and to be displayed when the structure is divided into a plurality of portions having the identical label to be displayed and is present in the three-dimensional image to be displayed by volume rendering.

Further, the three-dimensional image display apparatus according to the present invention may further include label adding means that adds at least one label to the three-dimensional image.

A three-dimensional image display method according to the present invention, of displaying a three-dimensional image of an object composed of a plurality of structures, to each of which at least one label is added, comprising:

displaying the three-dimensional image by volume rendering;

determining at least one label to be displayed from a plurality of labels based on the opacity of the three-dimensional image to be displayed by volume rendering; and adding the at least one label determined to be displayed to a corresponding structure and displaying the label with the three-dimensional image to be displayed by volume rendering.

Note that the three-dimensional image display method may be provided as a program for causing a computer to execute the three-dimensional image display method.

According to the present invention, when a three-dimensional image is displayed by volume rendering, the labels to be displayed are determined from among a plurality of labels based on the opacity of the three-dimensional image to be displayed by volume rendering, and then the labels determined to be displayed are added to the respective corresponding structures and displayed with the three-dimensional image. This enables the display of the labels added to the three-dimensional images to be controlled without the necessity of a user's operation, resulting in the burden on the user when displaying labels being reduced.

DESCRIPTION OF THE PREFERRED EMBODIMENTS

Figure 1:
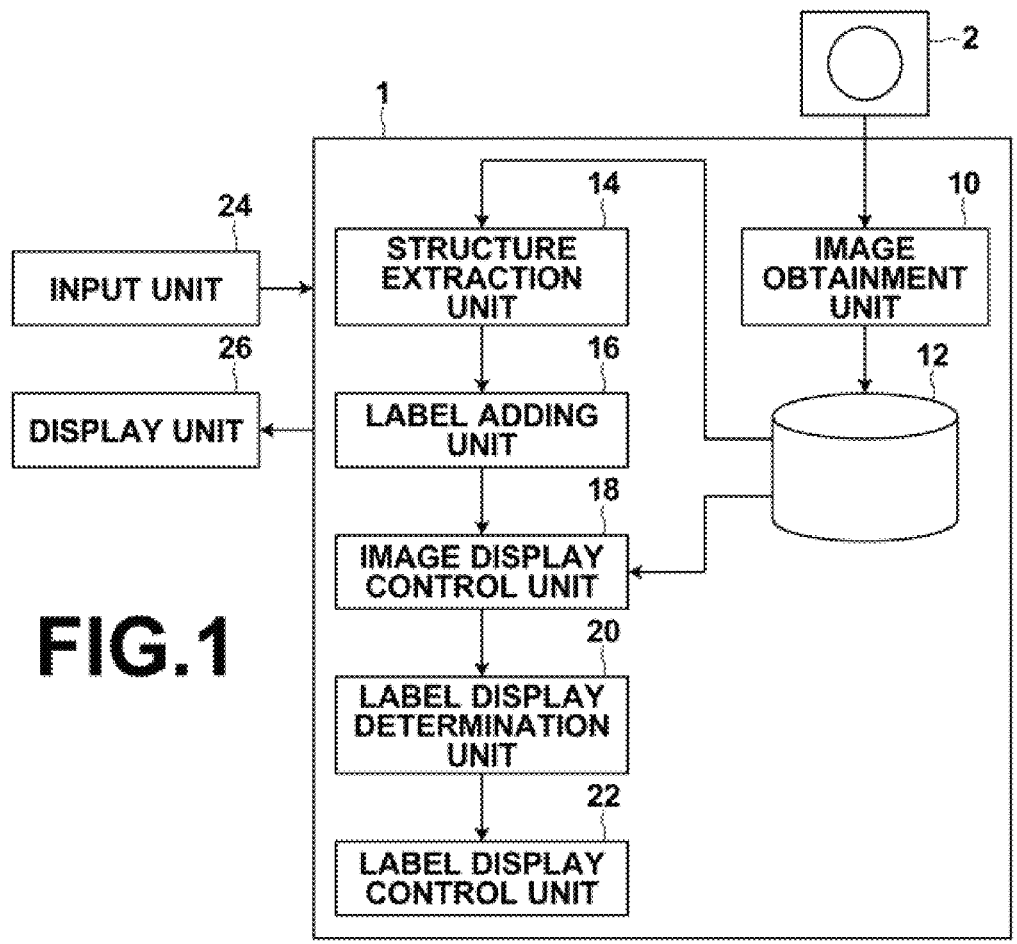
FIG. 1 is a block diagram that schematically illustrates the configuration of a three-dimensional image display apparatus of an embodiment of the present invention.

Hereinafter, an embodiment of the present invention will be described with reference to the drawings. FIG. 1 is a block diagram that schematically illustrates the configuration of a three-dimensional image display apparatus of an embodiment of the present invention. Note that the configuration of a three-dimensional image display apparatus 1 illustrated in FIG. 1 is realized by causing a three-dimensional image display program read into an auxiliary storage device to execute on a computer. This program is recorded in recording media such as CD-ROM's and the like or is distributed via a network such as the Internet to be installed in computers.

The three-dimensional image display apparatus 1 according to the present embodiment includes an image obtainment unit 10, a storage unit 12, a structure extraction unit 14, a label adding unit 16, an image display control unit 18, a label display determination unit 20, a label display control unit 22, an input unit 24 and a display unit 26.

The image obtainment unit 10 functions as a communication interface which obtains a three-dimensional image V0 acquired by imaging a chest of a subject in a modality 2 such as multi-slice CT apparatuses, MRI apparatuses, or the like. Note that the modality 2 is a multi-slice apparatus in this embodiment. Further, the three-dimensional image group V0 is delivered via a LAN from the modality 2.

Here, the three-dimensional image V0 is obtained by laminating two-dimensional tomographic images which are sequentially obtained along the direction perpendicular to the tomographic sections of the chest which is a target for diagnosis. In the present embodiment, the three-dimensional image V0 is generated by overlapping a plurality of tomographic images acquired by the modality 2. Note that a three-dimensional image which has been obtained by using the CT apparatus is data in which the amount of X-ray absorption is stored for each voxel (i.e., a pixel position) that constitutes lattice points in a three-dimensional space. In the data, one signal value (when the CT apparatus is applied for imaging, the value represents the amount of the X-ray absorption) is provided for each pixel position.

Note that the three-dimensional image V0 is added to with supplemental information specified by the DICOM (Digital Imaging and Communications in Medicine) specification. For examples, the supplemental information may include an image ID for identifying a three-dimensional image, a patient ID for identifying a subject, an examination ID for identifying an examination, a unique ID (UID) assigned to each piece of image information, the examination date on which the image information has been generated, the examination time, the kind of a modality which has been used in the examination to obtain the image information, information regarding the patient such as the name of the patient, age, gender, and the like, a site to be examined (a site to be imaged, a chest in the present embodiment), imaging conditions (whether contrast agent is used or not, the amount of radiation, and the like), a series number or an obtainment number when a plurality of images has been obtained for one examination.

The storage unit 12 is a large capacity storage device such as a hard disk and stores three-dimensional images V0 therein.

The structure extraction unit 14 extracts a body surface region, a lung region, a bronchus, and a pulmonary nodule from a three-dimensional image V0 of a chest, as structures. The body surface region is extracted by estimating the range of a signal value, in which a body surface is considered to be present, with respect to a signal value (i.e., CT value) at each pixel position of the three-dimensional image V0 and by performing threshold value processing using the estimated value of the range. A method for extracting the lung region, in which air is present in the lung field, may apply an arbitrary method such as a method in which a histogram of a signal value of each pixel position in the three-dimensional image V0 is generated and the lung region is subjected to the threshold processing, a region expanding method which is based on seed points that represent the lung region, and the like. The extracted lung region is then separated into five lobes: a right upper lobe, a right middle lobe, a right lower lobe, a left upper lobe and a left lower lobe. This separation may be performed by causing the display unit 26 to display the extracted lung field and by the user manually tracing interlobar membrane from the input unit 24. Alternatively, a method for automatically extracting interlobar membrane described in Y. Sato et al., "Extraction of Lung Lobes in X-ray CT images and its Application to Evaluation of Heavy Ion Radiation Therapy", MEDICAL IMAGING TECHNOLOGY, Vol. 22, No. 5, pp. 269-277, 2004, and the like may be applied. Note that the methods for extracting the lung region is not limited to these methods described above, but an arbitrary method may be applied.

A method for extracting the bronchus may be a method in which an assembly of pixels within the bronchus region is extracted by the region expanding method, and thinning processing is conducted on the extracted bronchus region. Further, in such a method, the respective pixels on thin lines are classified into end points, edges (sides), and branch points based on the connecting relationship of the thin lines that represent the obtained bronchus so that tree-structure data which represents the bronchus is obtained. Further, as described in N. Kawamura et al., "Examination of Bronchus Extraction Algorithm using Multi Slice CT Images", THE INSTITUTE OF ELECTRONICS, INFORMATION AND COMMUNICATION ENGINEERS, Technical Report, MBE, ME and bio-cybernetics, Vol. 105, No. 221, pp. 11-14, 2005, and the like, a method for automatically extracting the bronchus may be applied.

Further, in the present embodiment, anatomical nomenclature is performed for each bifurcation in the extracted bronchus. In this case, a user may perform such nomenclature manually. Alternatively, a method for automated nomenclature as described in K. Mori et al., "A method for automated nomenclature of bronchial branches extracted from CT images", International Congress Series, Vol. 1281, pp. 86-91, 2005, and the like may be applied. Through such methods, the right and left sides of the bronchus are named as apical branch (B1), posterior bronchus (B2), anterior bronchus (B3) . . . posterior basal (B10).

Methods for extracting pulmonary nodules as described in Y. Li et al., "Interactive Segmentation of Lung Nodules using AdaBoost and Graph Cuts", FOURTH INTERNATIONAL WORKSHOP ON PULMONARY IMAGE ANALYSIS, pp. 125-133, C. Schneider et al., "Automated lung nodule detection and segmentation", Medical Imaging, Proc. of SPIE, Vol. 7260, pp. 72601T1-1-72601T1-8, 2009, and the like may be applied. Alternatively, a user may manually extract pulmonary nodules by using the input unit 24.

The label adding unit 16 adds labels to the extracted structures in response to the user's input from the input unit 24. The contents of each label may include observations in addition to an anatomical name when the structure is a tumor, or the like. Alternatively, an arrow that represents the position of a tumor, or the like may be a label. In particular, a label describing the text "skin" is added to a body surface region, labels respectively describing the texts "right upper lobe", "right middle lobe", "right lower lobe", "left upper lobe", and "left lower lobe" are added to five lobes of a lung region, and a label describing the text "bronchus" is added to a bronchus region. Further, the anatomical nomenclature is performed on the bronchus in the present embodiment, and labels of the anatomical names, "B1" through "B10" are added to the bronchus accordingly. In addition, a label of an observation, indicating the text "a solid shade of 10 mm", is added to a pulmonary nodule region.

Note that, the addition of labels refers to mean that a plurality of pixels, which belong to an extracted structure in the three-dimensional image V0, are correlated to the text of a label. Such an operation enables the added label to be viewed when any one of the pixels included in the extracted structure is designated. Conversely, when the label is designated, the structure to which the label has been added will be viewed. The three-dimensional image V0 to which labels are added will be stored in the storage unit 12.

The image display control unit 18 displays a volume rendering (VR) image of a three-dimensional image V0 by using the volume rendering method. In other words, the image display control unit 18 emits a virtual light beam from a projection plane toward the three-dimensional image V0 and generates a three-dimensional image by virtual reflected light from the interior of the object, based on the colors (R, G, B) and opacity corresponding to the respective signal values in the three-dimensional image V0. Then, the image display control unit 18 further generates a projection image, which enables seeing through a three-dimensional structure in the interior of the object, on the projection plane from the three-dimensional image and displays this projection image as a volume rendering image. Note that the colors and opacity are defined in a predetermined color template, and the signal values at the respective pixel positions in the three-dimensional image V0 are converted into pixel values of the projection image, based on the colors and opacity set according to the predetermined color template by the alpha blending method. Note that during the display of the volume rendering (VR) image, when a user issues an instruction to change the color template or an instruction to change the opacity from the body surface toward the interior such that the structure of the interior of a chest is gradually displayed, the image display control unit 18 changes an aspect of the VR image of the three-dimensional image V0, based on the colors and opacity set according to a color template or based on a designated opacity.

The label display determination unit 20 determines a label/labels to be displayed together with a three-dimensional image to be displayed by VR (hereinafter referred to as a VR image) from a plurality of labels added to the three-dimensional image based on the opacity of the three-dimensional image V0 to be displayed by VR. Hereinafter, the process for determining label(s) to be displayed will be described.

In the present embodiment, colors for the pixels of a VR image are determined by the alpha blending method when displaying the VR image. In other words, a ray travels to the position where the ray attenuates to become 0, i.e., to the surface of an object while signal values within the three-dimensional image V0, which are present on the ray vector represented by the ray, and the values of the opacity respectively corresponding to the signal values are subjected to alpha blending with respect to pixels on the projection plane. The label display determination unit 20 calculates the distances between a pixel Pij of the surface of an object in the three-dimensional image V0 and pixels Li along the ray vector of the three-dimensional image V0. The pixels L1 are pixels in the interior of all of the structures to which labels are added. Then, the label display determination unit 20 calculates a pixel Li_min at which the distance to the pixel Pij is the shortest within each structure, and compares the calculated distance Dmin between the shortest point Li_min and the pixel Pij to a threshold value Th1 (for example, 1 cm). If the distance Dmin is less than or equal to the threshold value, label(s) added to the structure will be displayed.

Figure 2:
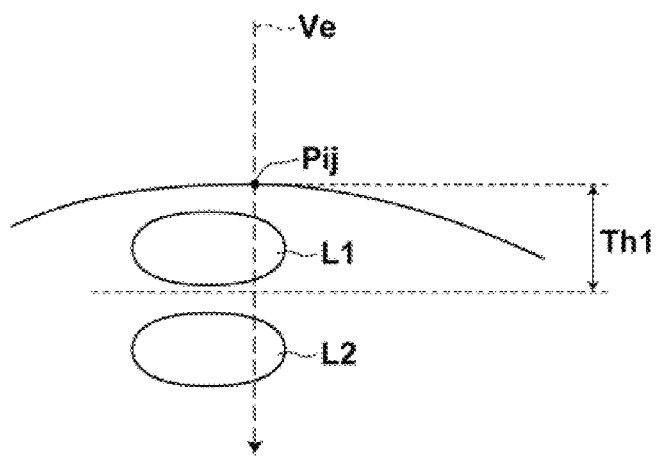
FIG. 2 is a diagram that describes the process for determining a label to be displayed.

FIG. 2 is a diagram that describes the process for determining a label to be displayed. Note that FIG. 2 illustrates a two-dimensional image to describe the process. As illustrated in FIG. 2, structures L1 and L2, to which labels are added, are disposed in this order along the ray vector Ve passing through a point Pij on the surface of an object. Further, if the distance between the pixel Pij on the surface and the structure L1 is less than or equal to the threshold value Th1 and the distance between the pixel Pij and the structure L2 exceeds the threshold Th1, the label display determination unit 20 will determine that label(s) added to the structure L1 are to be displayed.

All the pixels (x, y) of the surface over the projection plane are subjected to the process described above, and thereby a label map is generated, in which whether label(s) are displayed on the projection plane is defined. It is preferable for this label map to indicate 1 for each pixel (x, y) on the projection plane when label(s) are to be displayed and to indicate 0 for each pixel (x, y) on the projection plane when a label is not to be displayed. Further, pixels indicated as 1 are subjected to connected component processing and connected components composed of the pixels indicated as 1 are generated. Then, the number of pixels for each connected component is counted. If the number of the pixels is greater than or equal to a threshold value Th2 (for example, 100), label(s) added to a structure corresponding to the connected component will be determined to be displayed on a region composed of the connected component.

The label display control unit 22 overlays and displays label(s) added to a structure/structures corresponding to the connected component, label(s) added to which have been determined to be displayed, on a VR image being displayed. The position at which a label is displayed may be anywhere within the region of the connected component, the label added to which is to be displayed. However, when the position of the center of gravity of the connected component is within the connected component, the label should be displayed at the position. When the position of the center of gravity is not within the connected component, the label should be displayed at a position within the connected component, which is closest to the position of the center of gravity. The label may be displayed as it is at the display position. However, it is preferable for the label to be displayed with a reference line drawn from the display position. Further, when a plurality of labels are displayed, it is preferable for the labels to be displayed in the range that radially expands from the center of the VR image (i.e., the center of the projection plane).

Note that when the plurality of the labels are displayed, there are cases that display positions of the labels overlap with each other. In such a case, the label display control unit 22 moves the display position of the connected component having a larger area to a position where the labels do not overlap with each other, and thereby controls display of the labels so as to enable all the labels to be seen at the same time.

The input unit 24 includes a known input device such as a keyboard, a mouse, and the like.

The display unit 26 includes a known display device such as a liquid crystal, CRT, and the like.

Figure 3:
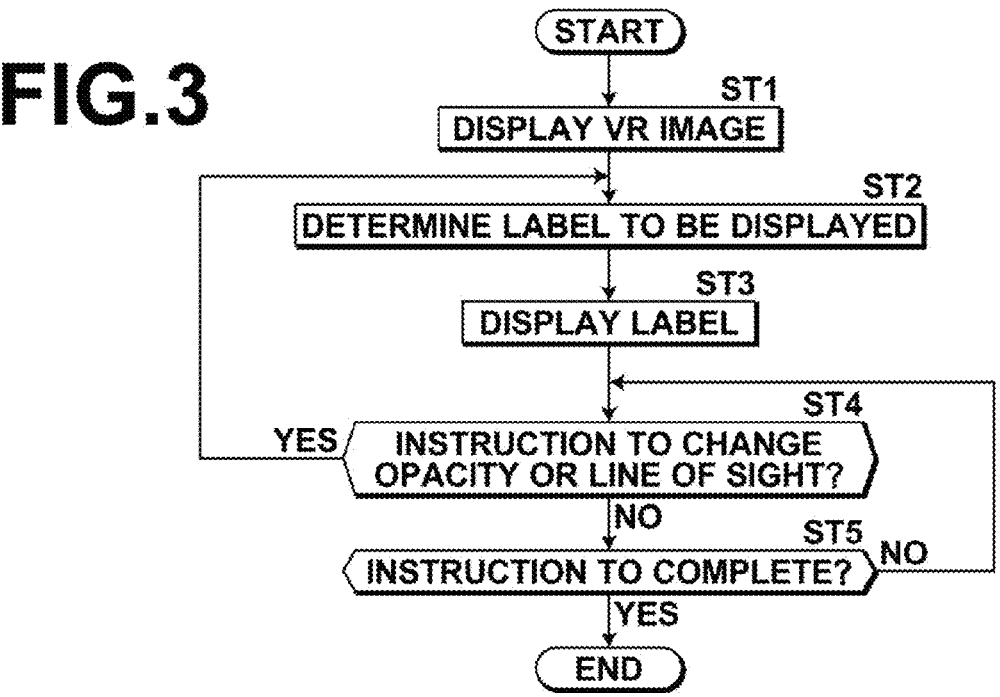
FIG. 3 is a flow chart that illustrates the process carried out in the present embodiment.

Next, the process carried out in the present invention will be described. FIG. 3 is a flow chart that illustrates the process carried out in the present embodiment. Note that the image obtainment unit 10 obtains the three-dimensional image V0, and the label adding unit 16 adds label(s) thereto before the storage unit 12 stores the three-dimensional image V0 therein. Further, the following will describe a case, in which a body surface is displayed, and then the opacity of the body surface is changed such that structures in the interior of the body surface will be sequentially displayed by VR. When a user operates the input unit 24, the image display control unit 18 causes the display unit 26 to display a VR image, onto which a structure/structures designated by the user have been projected (step ST1). Then, the label display determination unit 20 generates a label map as described above, and performs the connected composition processing to determine label(s) to be displayed (step ST2). Further, the label display control unit 22 displays label(s) on the VR image (step ST3).

Figure 4:
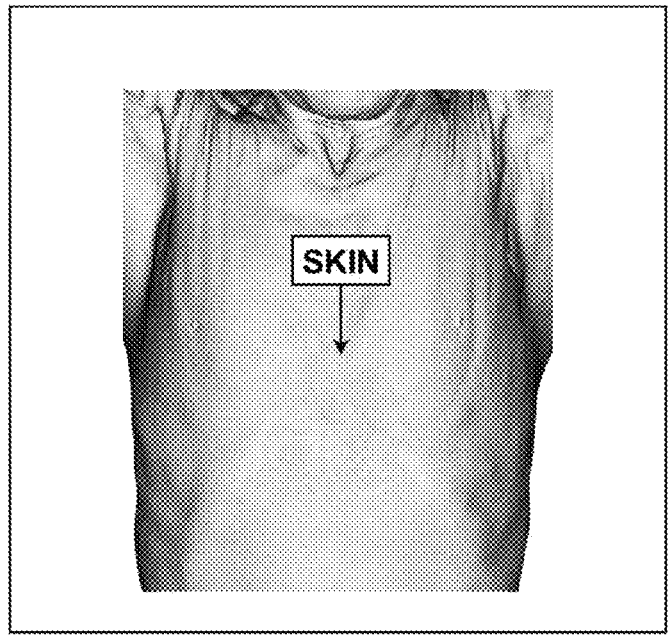
FIG. 4 is a diagram that illustrates a state in which a label is displayed in a VR image.

FIG. 4 is a diagram that illustrates a state in which a label is displayed in a VR image. The VR image of the body surface, which is opaque, is displayed in the first place. As illustrated in FIG. 4, the label of the text "skin" is displayed with a leader line drawn from the position of the center of gravity of the body surface. In this case, as the body surface is projected onto the substantially entire surface of the VR image, the leader line is drawn from the substantially center position of the VR image to display the label. Note that when the body surface is opaque, the organs in the interior thereof cannot be viewed.

Figure 5:
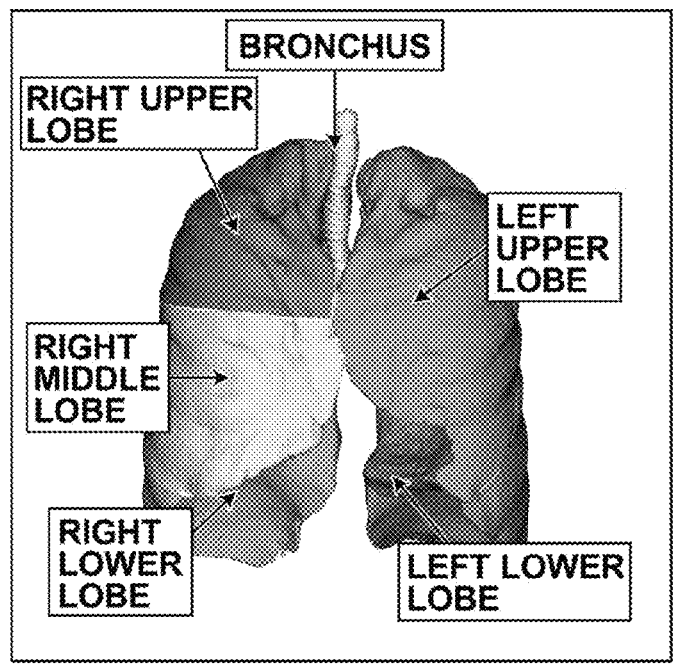
FIG. 5 is a diagram that illustrates a state in which the opacity of the body surface is changed in the VR image illustrated in FIG. 4.

In such a state, a determination is made whether an instruction to change the opacity or a line of sight is issued (step ST4). If an affirmative determination is made at ST4, the operation returns to step ST2 so that step ST2 and step ST3 will be repeated. If a user issues an instruction to gradually decrease the opacity of the body surface from the state illustrated in FIG. 2, the body surface in the VR image will gradually change from opaque to transparent. Then, the rays on the projection plane pass through the body surface and travel to the surface of the lung region and bronchus so that a VR image, onto which the lung region and bronchus are projected, will be displayed. In addition, labels are added to the respective five lobes of the lung region and the bronchus in the present embodiment. When the VR image of the surfaces of the lung region and the bronchus are displayed, the labels are added to the respective five lobes, which constitute the lung region, and the bronchus as illustrated in FIG. 5. Note that the labels are displayed with leader lines drawn from the position of the center of gravity of the respective five lobes and the bronchus, the leader lines being radially drawn with the center of the VR image as reference.

Further, if a user issues an instruction to change the opacity of the right upper lobe to be transparent, the portion of the right upper lobe will not be displayed and a VR image including the bifurcations of the bronchus, which were hidden under the right upper lobe, will be displayed instead. In this case, a VR image illustrated in FIG. 6 do not display the label of the right upper lobe, but displays the labels of the anatomical nomenclature B1 through B3 added to the bronchus and the label of the observation added to a pulmonary nodule which has been found in the bronchus.

Figure 6:
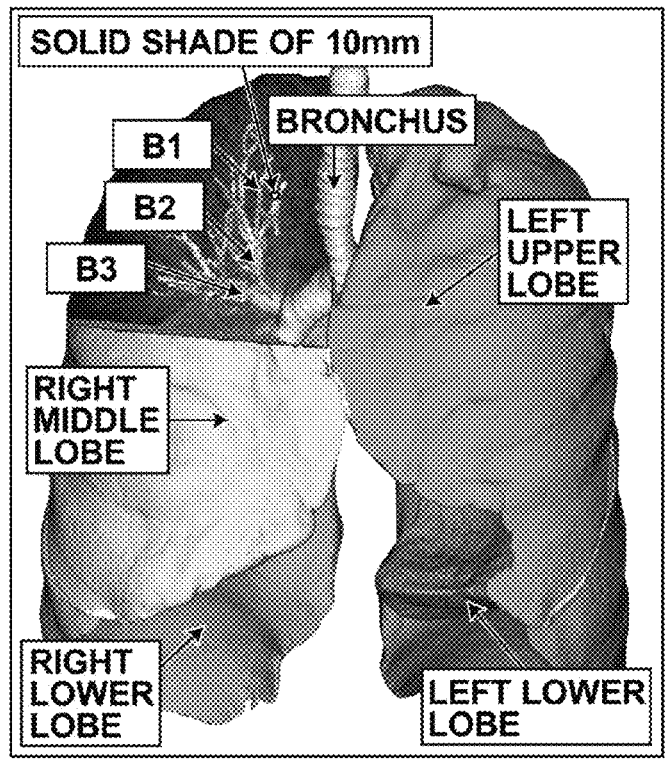
FIG. 6 is a diagram that illustrates a state in which the opacity of the right upper lobe is changed in the VR image illustrated in FIG. 5.
Figure 7:
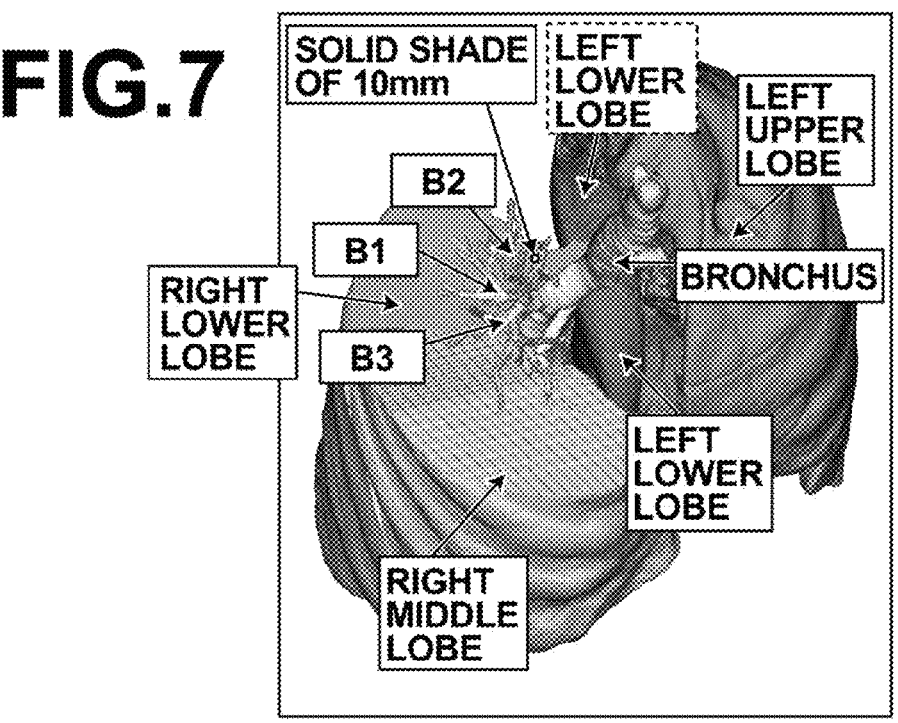
FIG. 7 is a diagram that illustrates a state in which a line of sight is changed in the VR image illustrated in FIG. 6.

The line of sight is changed and the projection plane is rotated from the state illustrated in FIG. 6 in such a manner to display a VR image with the lung region being observed from slightly upward. Then, it can be seen that left lower lobe is divided into two regions by the bronchus. In this case, the size of connected components (which have a value of 1) corresponding to the left lower lobe are compared to each other in the label map, and a larger region is added to with a label at the position of the center of gravity thereof and a smaller region is added to with a semitransparent label at the position of the center of gravity thereof. FIG. 7 illustrates this state. FIG. 7 represents the semitransparent label surrounded by the broken lines. Note that the label may be added only to the larger region, not to the smaller region.

Figure 8:
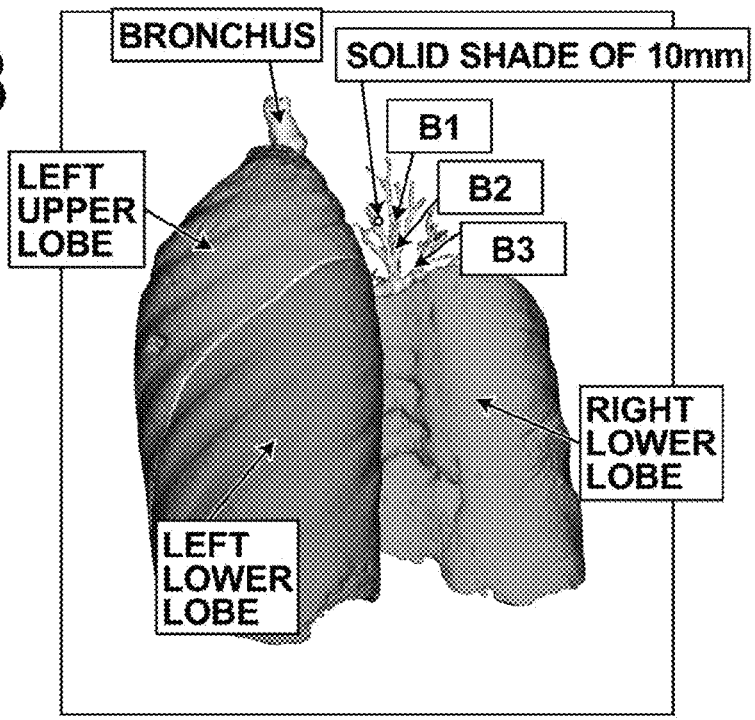
FIG. 8 is a diagram that illustrates a state in which a line of sight is changed in the VR image illustrated in FIG. 7.

Further, FIG. 8 illustrates a state in which a line of sight has been changed from the VR image illustrated in FIG. 7. FIG. 8 does not include the right middle lobe region. Therefore, the label of the right middle lobe is not to be displayed.

Returning to the flow chart, if a negative determination is made in step ST4, a determination is made whether an instruction to complete the process was issued (step ST5). If a negative determination is made in step ST5, the operation will return to step ST4. If an affirmative determination is made in step ST5, the process will be completed.

In such a manner as described above, in the present embodiment, label(s) to be displayed are determined from a plurality of labels based on the opacity when displaying a three-dimensional image V0 by VR. Then, label(s) determined to be displayed are added to a corresponding structure and displayed by VR together with the three-dimensional image V0. This enables the display of the labels added to the three-dimensional image V0 to be controlled without the necessity of a user's work, resulted in the burden on the user being reduced when displaying the labels.

Note that in the embodiment above, pulmonary arteries, pulmonary veins, ribs, and a spine may be extracted further and labels may be added thereto. In such a case as well, label(s) to be displayed are determined, and displayed with overlapped on the VR image in the same manner as described above.

Further, the process to be carried out for when a VR image of a lung region is displayed was described in the embodiment above. It is a matter of course that the present invention can be applied to the case in which a heart is extracted and a VR image of the heart region is displayed. Further, the present invention can be also applied to the case in which a three-dimensional image of an abdominal part is displayed. For example, a target in the abdominal part is designated as a liver region. The liver region, a hepatic an artery, a hepatic vein, a portal vein, and a tumor are extracted from the three-dimensional image V0, and a label is added to each of the liver region, hepatic an artery, hepatic vein, portal vein, and tumor. Labels to be displayed may be determined based on the opacity of structures to be displayed when the VR image is displayed.

Here, the heart region is extracted by estimating the range of a signal value, in which the heart is present in the three-dimensional image V0, and then carrying out threshold processing using the value of the range.

Further, a method for extracting the liver region may apply a method in which the range of CT values where the liver is present in the three-dimensional image V0 is estimated, the threshold processing is conducted by using the value of the range, and a morphology filter is applied to the extracted region. As described in J. Masumoto et al., "Automated Liver Segmentation Method for Dynamic CT Data Using Non-Rigid Registration", Journal of Computer Aided Diagnosis of Medical Images", Vol. 7, No. 4-1, pp. 29-38, 2003, a method in which contrast patterns of the liver region are detected by utilizing a plurality of phase images of the liver taken in chronological order and the liver region is detected by using the detected contrast patterns is also applied. Further, level set methods as described in P. S. Sulaiman et al., "A Liver Level Set (LLS) Algorithm for Extracting Liver's Volume Containing Disconnected Regions Automatically", IJCSNS International Journal of Computer Science and Network Security", Vol. 8, No. 12, pp. 246-252, 2008 and T. Hitosugi et al., "Development of a liver extraction method using a level set method and its performance evaluation", Computer Aided Diagnosis of Medical Images, Vol. 7, No. 4-2, pp. 1-9, 2003 can be applied. Note that the method for extracting the liver region of the present invention is not limited to these methods, but an arbitrary method may be applied.

Further, as a method for extracting a hepatic artery, a hepatic vein, and a portal vein (hereinafter, there are cases that these are referred to simply as blood vessels), a method in which a main axis direction and the positional information regarding a plurality of candidate points that represent a target tissue composed by a linear structure are calculated and the plurality of the candidate points are reconstructed to be connected with each other by using a cost function which is a variable based on the calculated positional information and main axis direction, as disclosed in Japanese Unexamined Patent Publication No. 2010-220742, for example may be applied. Further, a method for automatically discriminating blood vessels from each other and extracting them as disclosed in Japanese Unexamined Patent Publication No. 2011-212314 may also be applied.

Further, a method for extracting blood vessels may apply a method in which a tree-structure is generated by connecting the respective nodes with each other from a first root node corresponding to a first tree-structure root node and a second root node corresponding to a second tree-structure root node based on the characteristics of the blood vessels which repeatedly branch from an origin of each of a first and a second linear structures and extends in directions away from the origin in such a manner to become wider. In this method, a cost function is used such that a cost which represents ease of connection with respect to a plurality of edges, each of which is capable of connecting with each node, and which bind a plurality of nodes together is weighted for each node. Further, in this method, the first and second linear structures are designated as the hepatic artery and the hepatic vein, respectively so that the hepatic artery and the hepatic vein can be discriminated and extracted. Further, in this method, the first and second linear structures are designated as the portal vein and hepatic artery, and the hepatic vein, respectively so that the portal vein and hepatic artery, and the hepatic vein can be discriminated and extracted. Note that in this method, the origin may be identified by an arbitrary method, and the root node corresponding to the origin may be identified by a well-known method based on the origin. For example, the origin may be designated on a displayed image by an input device such as a mouse, or the like. Alternatively, an origin detection unit may be applied for detecting an origin. The origin detection unit detects the origin by mechanically learning a plurality of teacher data, which represents that the origin is a known predetermined structure. Note that various known methods for extracting a root node by mechanically learning teacher data may be applied. For example, the Adaboost method can detect an origin based on the amount of characteristics of a known origin in teacher data.

Further, a tumor can be extracted by methods that utilize the Voxel Classification described in M. Freiman et al., "Liver tumors segmentation from CTA images using voxels classification and affinity constraint propagation", Int J CARS, 2010. Note that methods for extracting hepatic arteries, hepatic veins, portal veins, and tumors are not limited to these methods, but an arbitrary method may be applied.

Further, the labels including the texts are displayed in the embodiments above. Only the arrows that represent the positions of tumors may be displayed as the labels.

The reproduction of the additional information when the additional information is added to the three-dimensional image of the human body was described in the embodiment mentioned above. It is a matter of course that the present invention can be applied to the case in which additional information is added to a three-dimensional image of the topography data, the case in which additional information is added to a three-dimensional image of cloud in the weather data, or the case in which additional information is added to three-dimensional images of various components in nondestructive inspection.

What is claimed is:

1. A three-dimensional image display apparatus that displays a three-dimensional image of an object composed of a plurality of structures, to each of which at least one label is added, comprising;
    an image display control unit that emits a virtual light beam from a projection plane toward the three-dimensional image, generates a three-dimensional image by virtual reflected light from the interior of the object, based on the colors (R, G, B) and opacity corresponding to the respective signal values in the three-dimensional image, and generates a projection image, which enables seeing through a three-dimensional structure in the interior of the object, on the projection plane from the three-dimensional image to display the three-dimensional image by volume rendering;
    a label display determination unit that determines at least one label to be displayed from a plurality of labels based on the opacity of the three-dimensional image to be displayed by volume rendering;
    a label display control unit that adds the at least one label determined to be displayed to a corresponding structure and displays the label with the three-dimensional image to be displayed by volume rendering.

2. The three-dimensional image display apparatus of claim 1, wherein the label display determination unit determines that labels added to structures are to be displayed in the case that the distance between a position at which the three dimensional image becomes opaque according to the opacity thereof and a structure to which a label has been added is less than or equal to a specified value.

3. The three-dimensional image display apparatus of claim 1, wherein the label display control unit controls the position of the at least one label to be displayed for each structure when the at least one label determined to be displayed is added to a plurality of structures.

4. The three-dimensional image display apparatus of claim 1, wherein the label display control unit causes the at least one label to be added only to a portion having a specified area or greater and displayed when the structure is divided into a plurality of portions having the identical label to be displayed and is present in the three-dimensional image to be displayed by volume rendering.

5. The three-dimensional image display apparatus of claim 1, wherein the label display control unit causes the at least one label to be added only to a portion having the largest area and to be displayed when the structure is divided into a plurality of portions having the identical label to be displayed and is present in the three-dimensional image to be displayed by volume rendering.

6. The three-dimensional image display apparatus of claim 1 that further comprises a label adding unit that adds at least one label to the three-dimensional image.

7. A three-dimensional image display method of displaying a three-dimensional image of an object composed of a plurality of structures, to each of which at least one label is added, comprising:
    displaying the three-dimensional image by emitting a virtual light beam from a projection plane toward the three-dimensional image, generating a three-dimensional image by virtual reflected light from the interior of the object, based on the colors (R, G, B) and opacity corresponding to the respective signal values in the three-dimensional image, and generating a projection image, which enables seeing through a three-dimensional structure in the interior of the object, on the projection plane from the three-dimensional image to display the three dimension image by volume rendering;
    determining at least one label to be displayed from a plurality of labels based on the opacity of the three-dimensional image to be displayed by volume rendering; and
    adding the at least one label determined to be displayed to a corresponding structure and displaying the label with the three-dimensional image to be displayed by volume rendering.

8. A non-transitory recording medium in which a program for causing a computer to execute a three-dimensional image display method for a three-dimensional image of an object composed of a plurality of structures, to each of which at least one label is added, has been recorded, comprising the steps of:
    displaying the three-dimensional image by emitting a virtual light beam from a projection plane toward the three-dimensional image, generating a three-dimensional image by virtual reflected light from the interior of the object, based on the colors (R, G, B) and opacity corresponding to the respective signal values in the three-dimensional image, and generating a projection image, which enables seeing through a three-dimensional structure in the interior of the object, on the projection plane from the three-dimensional image to display the three dimension image by volume rendering;

determining at least one label to be displayed from a plurality of labels based on the opacity of the three-dimensional image to be displayed by volume rendering; and adding the at least one label determined to be displayed to a corresponding structure and displaying the label with the three-dimensional image to be displayed by volume rendering.

* * * * *